United States Patent [19]
Bandman et al.

[11] Patent Number: 5,919,686
[45] Date of Patent: Jul. 6, 1999

[54] NADH DEHYDROGENASE SUBUNITS

[75] Inventors: Olga Bandman; Jennifer L. Hillman, both of Mountain View; Karl J. Guegler, Menlo Park; Purvi Shah, Sunnyvale, all of Calif.

[73] Assignee: Incyte Pharmaceuticals, Inc., Palo Alto, Calif.

[21] Appl. No.: 08/907,706

[22] Filed: Aug. 8, 1997

[51] Int. Cl.$^6$ .............................. C12N 9/06; C12N 15/00; C12N 15/85; C12Q 1/68
[52] U.S. Cl. ............................. 435/191; 435/6; 435/69.1; 435/320.1; 435/325; 536/23.1; 536/23.2
[58] Field of Search .................................... 435/69.1, 325, 435/6, 320.1, 191; 536/23.1, 23.2

[56] References Cited

PUBLICATIONS

Pla, M. et al., Mol. Gen. Genet., vol. 248, pp. 79–88 1995.
Kim, J. et al., Human NADH:ubiquinone oxidoreductase MLRQ subunit mRNA, complete cds, Genbank, Accession No: U94586 Apr. 22, 1997.
Cleeter, M.W., et al., "The polypeptide composition of the mitochondrial NADH: ubiquinone reductase complex from several mammalian species", *Biochem J*, 230:739–746 (1985).
Walker, J.E., et al., "Sequences of 20 Subunits of NADH: Ubiquinone Oxidoreductase from Bovine Heart Mitochrondria", *J Mol Biol*, 226:1051–1072 (1992). (GI 559) (GI 560).
Ali, S.T., et al., "Chromosomal Localization of the Human Gene Encoding the 51–kda Subunit of Mitochondrial Complex I (NDUFV1) to 11q13", *Genomics*, 18:435–439 (1993).
Fearnley, I.M., et al., "A homologue of the nuclear coded 49 kd subunit of bovine mitochondrial NADH–ubiquinone reductase is coded in chloroplast DNA", *The EMBO Journal*, 8:665–672 (1989). (GI 833) (GI 833783).
Singer, T.P., et al., "Deficiencies of NADH and succinate dehydrogenases in degenerative diseases and myopathies", *Biochimica et Biophysica Acta,* 1271: 211–219 (1995).
Selvanayagam, P., et al., "Detection of Mitochondrial Genome Depletion by a Novel Cdna in Real Cell Carcinoma", *Lab Invest,* 74:592–599 (1996).
Akman, S.A., et al., "DNA Base Modification Induced in Isolated Human Chromatin by Nadh Dehydrogenase–Catalyzed Reduction of Doxorubicin", *Biochemistry,* 31:3500–350*6 (1992).
Wilson, R., et al., "2.2 Mb of Contiguous nucleotide sequence from chromosome III of C. elegans", *Nature,* 368:32–38 (1994). (GI 470336) (GI 470339).
Wilson, R., et al., (GI 470336) GenBank Sequence Database (Accession U00043), National Center for Biotechnology Information: National Library of Medicine, Bethesda, Maryland 20849. (GI 470336) (GI 470339) (1994).
Tallquist, M.D., et al., (GI 1401251) GenBank Sequence Database (Accession U59509), National Center for Biotechnology Information: National Library of Medicine, Bethesda, Maryland 20849. (GI 1401251) (GI 1401252) (1996).

*Primary Examiner*—Robert A. Wax
*Assistant Examiner*—Peter P. Tung
*Attorney, Agent, or Firm*—Incyte Pharmaceuticals, Inc.

[57] ABSTRACT

The invention provides two human NADH dehydrogenase subunits (HNDS) and polynucleotides which identify and encode HNDS. The invention also provides expression vectors, host cells, agonists, antibodies and antagonists. The invention also provides methods for treating disorders associated with expression of HNDS.

20 Claims, 14 Drawing Sheets

5' NAG ATG GCG GCG CTG AGG GCT TTG TGC GGC TTC CGG GGC GTC GCG GCC CAG GTG
      M   A   A   L   R   A   L   C   G   F   R   G   V   A   A   Q   V

CTG CGG CCT GGG GCT GGA GTC CGA GTT CCG ATT CAG CCC AGC AGA GGT GTT CGG
 L   R   P   G   A   G   V   R   V   P   I   Q   P   S   R   G   V   R

CAG TGG CAG CCA GAT GTG GAA TGG GCA CAG CAG TTT GGG GGA GCT GTT ATG TAC
 Q   W   Q   P   D   V   E   W   A   Q   Q   F   G   G   A   V   M   Y

CCA AGC AAA GAA ACA GCC CAC TGG AAG CCT CCA TGG AAT CCT TGG AAT GTG GAC CCT
 P   S   K   E   T   A   H   W   K   P   P   W   N   P   W   N   D   P

CCA AAG GAC ACA ATT GTG AAG AAC ATT ACC CTG AAC TTT GGG CCC CAA CAC CCA
 P   K   D   T   I   V   K   N   I   T   L   N   F   G   P   Q   H   P

GCA GCG CAT GGT GTC CTG CGA CTA GTG ATG GAA TTG AGT GGG GAG ATG GTG CGG
 A   A   H   G   V   L   R   L   V   M   E   L   S   G   E   M   V   R

FIGURE 1A

```
                333         342         351         360         369         378
AAG TGT GAT CCT CAC ATC GGG CTC CTG CAC CGA GGC ACT GAG AAG CTC ATT GAA
 K   C   D   P   H   I   G   L   L   H   R   G   T   E   K   L   I   E 387         396         405         414         423         432
TAC AAG ACC TAT CTT CAG GCC CTT CCA TAC TTT GAC CGG CTA GAC TAT GTG TCC
 Y   K   T   Y   L   Q   A   L   P   Y   F   D   R   L   D   Y   V   S 441         450         459         468         477         486
ATG ATG TGT AAC GAA CAG GCC TAT TCT CTA GCT GTG GAG AAG TTG CTA AAC ATC
 M   M   C   N   E   Q   A   Y   S   L   A   V   E   K   L   L   N   I 495         504         513         522         531         540
CGG CCT CCT CGG GCA CAG TGG ATC CGA GTG CTG TTT GGA GAA ATC ACA CGT
 R   P   P   R   A   Q   W   I   R   V   L   F   G   E   I   T   R 549         558         567         576         585         594
TTG AAC CAC ATC ATG GCT GTG ACC ACA CAT GCC CTG GAC CTT GGG GCC ATG
 L   N   H   I   M   A   V   T   T   H   A   L   D   L   G   A   M 603         612         621         630         639         648
ACC CCT TTC TTC TGG CTG TTT GAA AGG GAG AAG ATG TTT GAG TTC TAC GAG
 T   P   F   F   W   L   F   E   E   R   E   K   M   F   E   F   Y   E
```

FIGURE 1B

```
      657           666           675           684           693           702
CGA GTG TCT GGA GCC CGA ATG CAT GCT TAT ATC CGG CCA GGA GGA GTG CAC
 R   V   S   G   A   R   M   H   A   Y   I   R   P   G   G   V   H 711           720           729           738           747           756
CAG GAC CTA CCC CTT ATG GAT GAC ATT TAT CAG TTT TCT AAG AAC TTC
 Q   D   L   P   L   M   D   D   I   Y   Q   F   S   K   N   F 765           774           783           792           801           810
TCT CTT CGG CTT GAT GAG TTG GAG TTG CTG ACC AAC AAT AGG ATC TGG CGA
 S   L   R   L   D   E   L   E   L   L   T   N   N   R   I   W   R 819           828           837           846           855           864
AAT CGG ACA ATT GAC ATT GGG GTT GTA ACA GCA GAA GAA GCA CTT AAC TAT GGT
 N   R   T   I   D   I   G   V   V   T   A   E   E   A   L   N   Y   G 873           882           891           900           909           918
TTT AGT GGA GTG ATG CTT CGG GGC ATC CAG TGG GAC CTG CGG AAG ACC
 F   S   G   V   M   L   R   G   I   Q   W   D   L   R   K   T 927           936           945           954           963           972
CAG CCC TAT GAT GTT TAC GAC CAG GTT GAG TTT GAT GTT CCT GTT GGT TCT CGA
 Q   P   Y   D   V   Y   D   Q   V   E   F   D   V   P   V   G   S   R
```

FIGURE 1C

```
      981         990         999        1008        1017        1026
GGG GAC TGC TAT GAT AGG TAC CTG TGC CGG GTG GAG GAG ATG CGC CAG TCC CTG
 G   D   C   Y   D   R   Y   L   C   R   V   E   E   M   R   Q   S   L 1035        1044        1053        1062        1071        1080
AGA ATT ATC GCA CAG TGT CTA AAC AAG ATG CCT CCT GGG GAG ATC AAG GTT GAT
 R   I   I   A   Q   C   L   N   K   M   P   P   G   E   I   K   V   D 1089        1098        1107        1116        1125        1134
GAT GCC AAA GTG TCT CCA CCT AAG CGA GCA GAG ATG AAG ACT TCC ATG GAG TCA
 D   A   K   V   S   P   P   K   R   A   E   M   K   T   S   M   E   S 1143        1152        1161        1170        1179        1188
CTG ATT CAT CAC TTT AAG TTG TAT ACT GAG GGC TAC CAA GTT CCT CCA GGA GCC
 L   I   H   H   F   K   L   Y   T   E   G   Y   Q   V   P   P   G   A 1197        1206        1215        1224        1233        1242
ACA TAT ACT GCC ATT GAG GCT CCC AAG GGA GAG TTT GGG GTG TAC CTG GTG TCT
 T   Y   T   A   I   E   A   P   K   G   E   F   G   V   Y   L   V   S 1251        1260        1269        1278        1287        1296
GAT GGC AGC AGC CGC CCT TAT CGA TGC AAG ATC AAG GCT CCT GGT TTT GCC CAT
 D   G   S   S   R   P   Y   R   C   K   I   K   A   P   G   F   A   H
```

FIGURE 1D

```
      1305           1314           1323           1332           1341           1350
CTG GCT GGT TTG GAC AAG ATG TCT AAG GGA CAC ATG TTG GCA GAT GTC GTT GCC
 L   A   G   L   D   K   M   S   K   G   H   M   L   A   D   V   V   A 1359           1368           1377           1386           1395           1404
ATC ATA GGT ACC CAA GAT ATT GTA TTT GGA GAA GTA GAT CGG TGA GCA GGG GAG
 I   I   G   T   Q   D   I   V   F   G   E   V   D   R 1413           1422           1431           1440           1449           1458
CAG CGT TTG ATC CCC CCT GCC TAT CAG CTT CTG TGG AGC CTG TTC CTC ACT 1467           1476           1485           1494           1503           1512
GGA AAT TGG CCT CTG TGT GTG TGT GTG TGT GTG TGT GTG TGT GTA TGT 1521           1530           1539           1548           1557
TCA TGT ACA CTT GGC TGT CAG GCT TTC TGT GCA TGT ACT AAA AAA AAA A 3'
```

FIGURE 1E

```
5' NCG CTG GCC CGG CCC ACC CGG GGC TGT GGT TAT ATA TAA GGT GGG GAG
     9              18          27       36       45          54

GCC GCC GGC CCG TTC GGT TCC GGG CGT TAC CAT CGT CCG TGC CCC GGC
     63          72          81          90          99       108

GTC CAG ATT TGG CAA TTC TTC GCT GAA GTC ATC ATG AGC TTT CAA CTC CTG
    117         126         135         144         153        162
                                         M   S   F   Q   L   L

ATG AAA AGG AAG GAA CTC ATT CCC TTG GTG GTG TTC ATG ACT GTG GCG GCG GGT
    171         180         189         198         207         216
 M   K   R   K   E   L   I   P   L   V   V   F   M   T   V   A   A   G

GGA GCC TCA TCT TTC GCT GTG TAT TCT CTT TGG AAA ACC GAT GTG ATC CTT GAT
    225         234         243         252         261         270
 G   A   S   S   F   A   V   Y   S   L   W   K   T   D   V   I   L   D

CGA AAA AAT CCA GAA CCT TGG GAA ACT GTG GAC CCT ACT GTA CCT CAA AAG
    279         288         297         306         315        324
 R   K   N   P   E   P   W   E   T   V   D   P   T   V   P   Q   K
```

FIGURE 2A

```
       333         342         351         360         369         378
CTT ATA ACA ATC AAC CAA CAA TGG AAA CCC ATT GAA GAG TTG CAA AAT GTC CAA
 L   I   T   I   N   Q   Q   W   K   P   I   E   E   L   Q   N   V   Q 387         396         405         414         423         432
AGG GTG ACC AAA TGA CGA GCC CTC GCC TCT TTC TGA AGA GTA CTC TAT AAA
 R   V   T   K 441         450         459         468         477         486
TCT AGT GGA AAC ATT TCT GCA CAA ACT AGA TTC TGG ACA CCA GTG TGC GGA AAT 495         504         513         522         531         540
GCT TCT GCT ACA TTT TTA GGG TTT GTC TAC ATT TTT TGG GCT CTG GAT AAG GAA 549         558         567
TTA AAG GAG TGC AGC AAT AAC TGC ACT GTC T 3'
```

FIGURE 2B

| | | | |
|---|---|---|---|
| 1 | M A A L R A L C G F R G V A - - - - - - - - - - - - - - A Q V L R P G A G V R L P I Q P - S R G V R | HNDS-1 |
| 1 | - - - - - - - - - - - - - - - - - - - - - - - - - - - - - - - - - - - - - - - - | g833783 |
| 1 | M L S - R S L H P L R A V A C A R P A I S N R D S H T I W Y P D A K F E R Q F K | g470339 |
| 36 | Q - - - - - - - W Q P D V E W A Q Q F G G A V M Y P S K E T A H W K P P P W N D | HNDS-1 |
| 1 | Q - - - - - - - W Q P D V E W A E Q Y G G A V M Y P T K E T A H W K P P P W N D | g833783 |
| 40 | T G G T L G K L W M S - - E R V S D F D D Q I G L D K L E K L A Y S D P V L S D | g470339 |
| 69 | V - - D P P K D T I V K N I T L N F G P Q H P A A H G V L R L V M E L S G E M V | HNDS-1 |
| 34 | V - - D P P K D T L V S N L T L N F G P Q H P A A H G V L R L V M E L S G E M V | g833783 |
| 78 | N Y E G K K R E K N L E N M I L N F G P Q H P A A H G V L R L V L K L E G E V I | g470339 |
| 107 | R K C D P H I G L L H R G T E K L I E Y K T Y L Q A L P Y F D R L D Y V S M M C | HNDS-1 |
| 72 | R K C D P H I G L L H R G T E K L I E Y K T Y L Q A L P Y F D R L D Y V S M M C | g833783 |
| 118 | I K A I P H I G L L H R A T E K L I E H K T Y T Q A L P Y F D R L D Y V S M M C | g470339 |
| 147 | N E Q A Y S L A V E K L L N I R P P P R A Q W I R V L F G E I T R L L N H I M A | HNDS-1 |
| 112 | N E Q A Y S L A V E K L L N I R P P P R A Q W I R V L F G E I T R L L N H I M A | g833783 |
| 158 | N E Q A F S L A I E K L L G I D V P P R A K Y I R I L F G E L T R I Q N H I M G | g470339 |
| 187 | V T T H A L D L G A M T P F F W L F E E R E K M F E F Y E R V S G A R M H A A Y | HNDS-1 |
| 152 | V T T H A L D I G A M T P F F W M F E E R E K M F E F Y E R V S G A R M H A A Y | g833783 |
| 198 | I T T H A L D V G A M T P F F W M F E R E K L F E F S E R V S G A R M H A N Y | g470339 |

FIGURE 3A

```
227 I R P G G V H Q D L P L G L M D D I Y Q F S K N F S L R L D E L E E L L T N N R   HNDS-1
192 V R P G G V H Q D L P L G L M D D I Y E F S K N F S L R I D E L E E M L T N N R   g833783
238 V R P G G V A W D L P V G L M D D I Y D W A V K F P A R I D E L E D M L T E N R   g470339

267 I W R N R T I D I G V V T A E E A L N Y G F S G V M L R G S G I Q W D L R K T Q   HNDS-1
232 I W R N R T V D I G I V T A E D A L N Y G F S G V M L R G S G I Q W D L R K T Q   g833783
278 I W K A R T V D I G L V S A S D A L N W G F S G V M V R G S G I K Q D V R K T E   g470339

307 P Y D V Y D Q V E F D V P V G S R G D C Y D R Y L C R V E E M R Q S L R I I A Q   HNDS-1
272 P Y D V Y D Q V E F D V P I G S R G D C Y D R Y L C R V E E M R Q S I R I I S Q   g833783
318 P Y D A Y A D M E F D V P I G T K G D C Y D R Y L C R V E E M R Q S L N I V H Q   g470339

347 C L N K M P P G E I K V D D A K V S P P K R A E M K T S M E S L I H H F K L Y T   HNDS-1
312 C L N K M P P G E I K V D D A K V S P P K R A E M K T S M E S L I H H F K L Y T   g833783
358 C L N K M P T G E I K S D D H K V P P K R A E M K E N M E S L I H H F K F F T   g470339

387 E G Y Q V P P G A T Y T A I E A P K G E F G V Y L V S D G S S R P Y R C K I K A   HNDS-1
352 E G Y Q V P P G A T Y T A I E A P K G E F G V Y L V S D G S S R P Y R C K I K A   g833783
398 E G F Q V P P G A T Y V P I E A P K G E F G V Y L V A D G T G K P Y R C F I R A   g470339

427 P G F A H L A G L D K M S K G H M L A D V V A I I G T Q D I V F G E V D R   HNDS-1
392 P G F A H L A G L D K M S K G H M L A D V V A I I G T Q D I V F G E V D R   g833783
438 P G F A H L A A I H D V C Y M S L I A D I V A V I G T M D I V F G E V D R   g470339
```

FIGURE 3B

```
  1 M - - S F F Q L L M R R K E L I P L V V F M T V A A G G A S S F A V - Y S L W K  HNDS-2
  1 M L R Q I I G Q A K R H P S L I P L F I F I G A G G T G A A L Y V T R L A L F N  g560
  1 - - - - - Q A K K H P S L I P L F V F I G A G G T G A A L Y V M R L A L F N     g1401252

38 T D V I L D R K K N P E P W E T V D P T V P Q K L I T I N Q Q W K P I E E L Q N  HNDS-2
 41 P D V S W D R K N N P E P W N K L G P N D Q Y K F Y S V N V D Y S K L K K - - -  g560
 34 P D V S W D R K N N P E P W N K L G P N E Q Y K F Y S V N V D Y S K L K K - - -  g1401252

78 V Q R V T K                                                                     HNDS-2
 78 - E G P D F                                                                     g560
 71 - E G P D F                                                                     g1401252
```

FIGURE 4

NADH DEHYDROGENASE SUBUNITS

FIELD OF THE INVENTION

This invention relates to nucleic acid and amino acid sequences of NADH dehydrogenase subunits and to the use of these sequences in the diagnosis, prevention, and treatment of cancer and immune and smooth muscle disorders.

BACKGROUND OF THE INVENTION

NADH dehydrogenase (NADH:ubiquinone oxidoreductase, NADH-D) is the first multienzyme complex (Complex I) in a chain of three complexes that make up the mitochondrial electron transport chain. The mitochondrial electron transport chain is responsible for the transport of electrons from NADH to oxygen and the coupling of this oxidation to the synthesis of ATP (oxidative phosphorylation) which provides the energy source for driving a cell's many energy-requiring reactions. NADH-D accomplishes the first step in this process by accepting electrons from NADH and passing them through a flavin molecule to ubiquinone, which transfers the electrons to the second enzyme complex in the chain.

NADH-D and the other members of the electron transport chain are located in the mitochondrial membrane. NADH-D is the largest of the three complexes with an estimated mass of 800 kDa comprising some 40 polypeptide subunits of widely varying size and composition. The polypeptide composition of NADH-D in a variety of mammalian species including rat, rabbit, cow, and man is very similar (Cleeter, M. W. J. and Ragan, C. I. (1985) Biochem. J. 230: 739–746). The best characterized NADH-D is from bovine heart mitochondria and is composed of 41 polypeptides (Walker, J. E. et al. (1992) J. Mol. Biol. 226: 1051–1072). Seven of these polypeptides are encoded by mitochondrial DNA while the remaining 34 are nuclear gene products that are imported into the mitochondria. Many of these imported polypeptides are characterized by various N-terminal peptide sequences that target them to the mitochondria and are then cleaved from the mature protein. A second group of polypeptides have neither N-terminal targeting sequences nor modified-N terminal amino acids. The import signals of this second group appear to be lie within the mature protein (Walker et al., supra).

The functions of many of the individual subunits in NADH-D are largely unknown. The 24-, 51-, and 75-kDa subunits have been identified as being catalytically important in electron transport, with the 51-kDa subunit forming part of the NADH binding site and containing the flavin moiety that is the initial electron acceptor (Ali, S. T. et al. (1993) Genomics 18:435–39). The location of other functionally important groups, such as the electron-carrying iron-sulfate centers, remains to be determined. Many of the smaller subunits (<30 kDa) contain hydrophobic sequences that may be folded into membrane spanning α-helices. These subunits presumably are anchored into the inner membrane of the mitochondria and interact via more hydrophilic parts of their sequence with globular proteins in the large extrinsic domain of NADH-D.

The 49 kDa subunit of bovine NADH-D is associated with the iron-sulfate portion of the complex (Fearnley, I. M. et al. (1989) EMBO J. 8:665–72). Although the 49 kDa subunit is a nuclear encoded polypeptide that is isolated together with a 30 kDa and a 13 kDa subunit, the function of the 49 kDa subunit is not known. The three proteins (13-, 30-, and 49-kDa) contain two iron-sulfur centers among them. However, no cysteine-containing motifs typical of iron-sulfate centers are found in the 49 kDa subunit, so there is no evidence that it contains one of the iron-sulfur centers. The 49 kDa subunit may be a transmembrane protein but it contains only one hydrophobic region of sufficient length to span the typical membrane (Fearnley et al. supra).

The MLRQ subunit is one of the small (9 kDa) subunits that is nuclear encoded and contains no signal peptide (Walker et al. supra). A potential membrane-spanning α-helix presumably anchors the MLRQ subunit to the inner membrane of the midtochondria, but the precise function of the subunit is unknown.

Defects and altered expression of NADH-D are associated with a variety of disease conditions in man, including neurodegenerative diseases, myopathies, and cancer (Singer, T. P. et al. (1995) Biochim. Biophys. Acta 1271:211–19; Selvanayagam, P. and Rajaraman, S. (1996) Lab. Invest. 74:592–99). In addition, NADH-D reduction of the quinone moiety in chemotherapeutic agents such as doxorubicin is believed to contribute to the antitumor activity and/or mutagenicity of these drugs (Akman, S. A. et al. (1992) Biochemistry 31:3500–6).

The discovery of new NADH-D subunits and the polynucleotides encoding them satisfies a need in the art by providing new compositions which are useful in the diagnosis, prevention and treatment of cancer and immune and smooth muscle disorders.

SUMMARY OF THE INVENTION

The invention features two substantially purified polypeptides, NADH-D subunits (designated individually as HNDS-1 and HNDS-2, and collectively as HNDS), having the amino acid sequences shown in SEQ ID NO:1 or SEQ ID NO:3, respectively, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1 or fragments of said polynucleotide sequence. The invention further provides a polynucleotide sequence comprising the complement of the polynucleotide sequence encoding the amino acid sequence of SEQ ID NO:1 or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2 or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding HNDS-1 under conditions suitable for the expression of the polypeptide; and b) recovering the polypeptide from the host cell culture.

The invention also provides a pharmaceutical composition comprising a substantially purified HNDS-1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for treating or preventing a smooth muscle disorder comprising administering to a subject in need of such treatment an effective amount of a pharmaceutical composition comprising purified HNDS-1.

The invention also provides a method for treating or preventing cancer comprising administering to a subject in need of such treatment an effective amount of a purified antagonist of HNDS-1.

The invention also provides a method for treating or preventing an immune disorder comprising administering to a subject in need of such treatment an effective amount of a purified antagonist of HNDS-1.

The invention also provides a method for detecting a polynucleotide which encodes HNDS-1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding HNDS-1 in the biological sample. In one aspect the nucleic acid material of the biological sample is amplified by the polymerase chain reaction prior to hybridization.

The invention further provides an isolated and substantially purified polynucleotide sequence encoding the polypeptide comprising the amino acid sequence of SEQ ID NO:3 or fragments thereof and a composition comprising said polynucleotide sequence. The invention also provides a polynucleotide sequence which hybridizes under stringent conditions to the polynucleotide sequence encoding the amino acid sequence SEQ ID NO:3 or fragments of said polynucleotide sequence. The invention further provides a polynucleotide sequence comprising the complement of the polynucleotide sequence encoding the amino acid sequence of SEQ ID NO:3 or fragments or variants of said polynucleotide sequence.

The invention also provides an isolated and purified sequence comprising SEQ ID NO:4 or variants thereof. In addition, the invention provides a polynucleotide sequence which hybridizes under stringent conditions to the polynucleotide sequence of SEQ ID NO:4. The invention also provides a polynucleotide sequence comprising the complement of SEQ ID NO:4, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3 or a fragment thereof, the method comprising the steps of: a) culturing the host cell containing an expression vector containing at least a fragment of the polynucleotide sequence encoding HNDS-2 under conditions suitable for the expression of the polypeptide; and b) recovering the polypeptide from the host cell culture.

The invention also provides a pharmaceutical composition comprising a substantially purified HNDS-2 having the amino acid sequence of SEQ ID NO:3 in conjunction with a suitable pharmaceutical carrier.

The invention also provides a purified antagonist of the polypeptide of SEQ ID NO:3. In one aspect the invention provides a purified antibody which binds to a polypeptide comprising the amino acid sequence of SEQ ID NO:3.

Still further, the invention provides a purified agonist of the polypeptide of SEQ ID NO:3.

The invention also provides a method for treating or preventing a smooth muscle disorder comprising administering to a subject in need of such treatment an effective amount of a pharmaceutical composition comprising purified HNDS-2.

The invention also provides a method for treating or preventing cancer comprising administering to a subject in need of such treatment an effective amount of a purified antagonist of HNDS-2.

The invention also provides a method for treating or preventing an immune disorder comprising administering to a subject in need of such treatment an effective amount of a purified antagonist of HNDS-2.

The invention also provides a method for detecting a polynucleotide which encodes HNDS-2 in a biological sample comprising the steps of: a) hybridizing the complement of the polynucleotide sequence which encodes SEQ ID NO:3 to nucleic acid material of a biological sample, thereby forming a hybridization complex; and b) detecting the hybridization complex, wherein the presence of the complex correlates with the presence of a polynucleotide encoding HNDS-2 in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of HNDS-1. The alignment was produced using MACDNASIS PRO software (Hitachi Software Engineering Co. Ltd. San Bruno, Calif.).

FIGS. 2A and 2B show the amino acid sequence (SEQ ID NO:3) and nucleic acid sequence (SEQ ID NO:4) of HNDS-2. The alignment was produced using MACDNASIS PRO software.

FIGS. 3A and 3B show the amino acid sequence alignments among HNDS-1 (SEQ ID NO:1), the 49 kDa NADH-D subunit from cow (GI 833783; SEQ ID NO:5), and a similar subunit from *Caenorhabditis elegans* (GI 470339; SEQ ID NO:6), produced using the multisequence alignment program of DNASTAR™ software (DNASTAR Inc, Madison Wis.).

FIG. 4 shows the amino acid sequence alignments among HNDS-2 (SEQ ID NO:3), the MLRQ subunit of NADH-D from cow (GI 560; SEQ ID NO:7), and an MLRQ-like protein from mouse (GI 1401252; SEQ ID NO:8), produced using the multisequence alignment program of DNASTAR™ software.

DESCRIPTION OF THE INVENTION

Figure 5A:
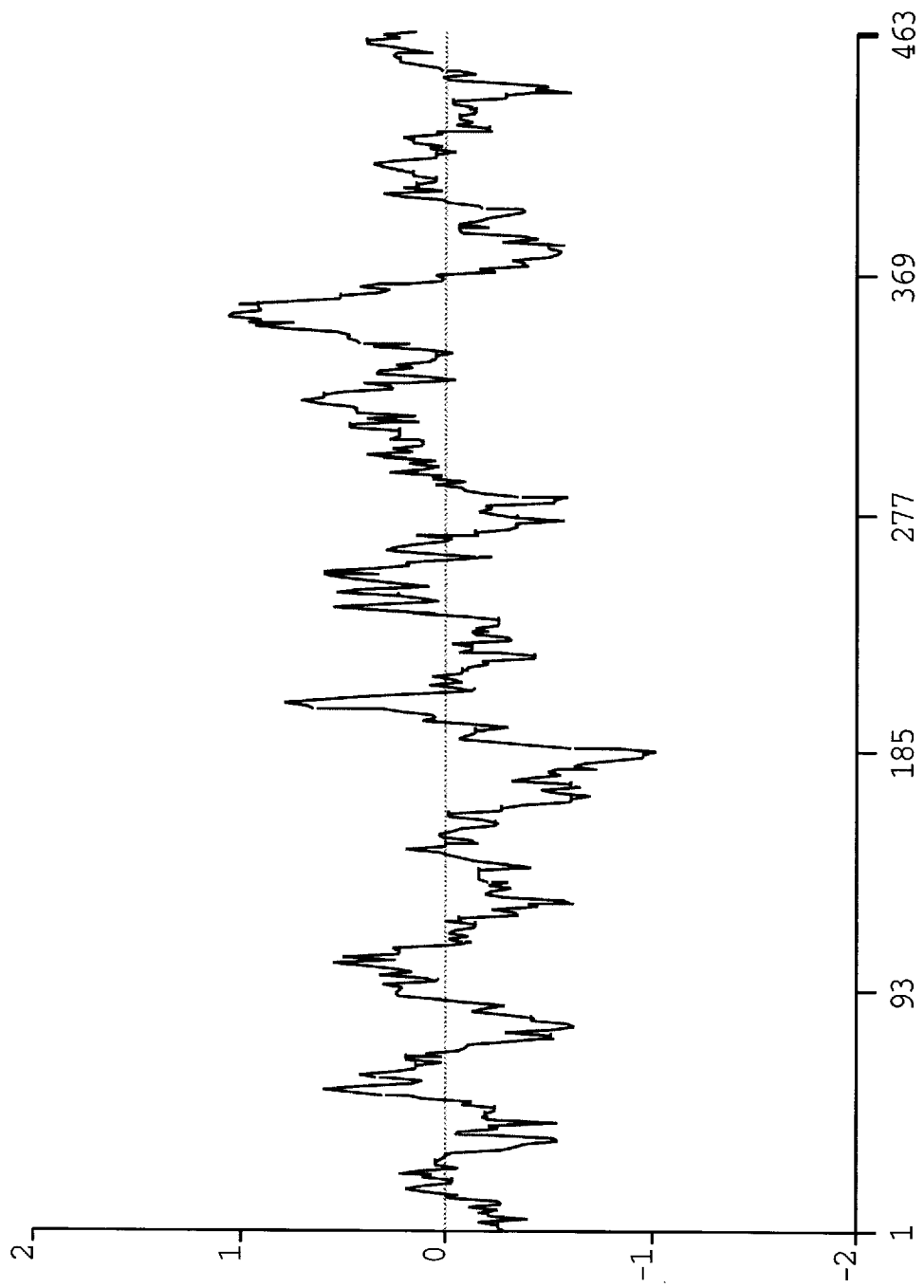
FIGS. 5A and 5B show the hydrophobicity plots for HNDS-1 (SEQ ID NO:1) and the bovine 49 kDa subunit (SEQ ID NO:5), respectively; the positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

HNDS, as used herein, refers to the amino acid sequences of substantially purified HNDS obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to HNDS, increases or prolongs the duration of the effect of HNDS. Agonists may include proteins, nucleic acids, carbohydrates, or any other molecules which bind to and modulate the effect of HNDS.

An "allele" or "allelic sequence", as used herein, is an alternative form of the gene encoding HNDS. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HNDS as used herein include those with deletions, insertions, or substitutions of different nucleotides resulting in a polynucleotide that encodes the same or a functionally equivalent HNDS. Included within this definition are polymorphisms which may or may not be readily detectable using a particular oligonucleotide probe of the polynucleotide encoding HNDS, and improper or unexpected hybridization to alleles, with a locus other than the normal chromosomal locus for the polynucleotide sequence encoding HNDS. The encoded protein may also be "altered" and contain deletions, insertions, or substitutions of amino acid residues which produce a silent change and result in a functionally equivalent HNDS. Deliberate amino acid substitutions may be made on the basis of similarity in polarity, charge, solubility, hydrophobicity, hydrophilicity, and/or the amphipathic nature of the residues as long as the biological or immunological activity of HNDS is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of HNDS are preferably about 5 to about 15 amino acids in length and retain the biological activity or the immunological activity of HNDS. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to HNDS, decreases the amount or the duration of the effect of the biological or immunological activity of HNDS. Antagonists may include proteins, nucleic acids, carbohydrates, antibodies or any other molecules which decrease the effect of HNDS.

As used herein, the term "antibody" refers to intact molecules as well as fragments thereof, such as Fab, F(ab')$_2$, and Fv, which are capable of binding the epitopic determinant. Antibodies that bind HNDS polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic HNDS, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding HNDS (SEQ ID NO:1 or SEQ ID NO:3) or fragments thereof (e.g., SEQ ID NO:2 or SEQ ID NO:4 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.). "Consensus", as used herein, refers to a nucleic acid sequence which has been resequenced to resolve uncalled bases, has been extended using the XL-PCR Klt (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 or SEQ ID NO:4 by northern analysis is indicative of the presence of mRNA encoding HNDS in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to HNDS or the encoded HNDS. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of HNDS. For example, modulation may cause an increase or a decrease in protein activity, binding characteristics, or any other biological, functional or immunological properties of HNDS.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length HNDS-1 and fragments thereof.

The term "sample", as used herein, is used in its broadest sense. A biological sample suspected of containing nucleic acid encoding HNDS, or fragments thereof, or HNDS itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of HNDS, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of new human NADH-H subunits (hereinafter referred to collectively as "HNDS" and individually as HNDS-1 and HNDS-2), the polynucleotides encoding HNDS, and the use of these compositions for the diagnosis, prevention, or treatment of cancer and immune and smooth muscle disorders.

Nucleic acids encoding HNDS-1 of the present invention were first identified in Incyte Clone 13705 from the promonocyte cell cDNA library (THP1PLB01) using a computer search for amino acid sequence alignments. A consensus sequence, SEQ ID NO:2, was derived from the following overlapping and/or extended nucleic acid sequences: Incyte Clones 13705 (THP1PLB01), 483916 (HNT2RAT01), 1720783 (BLADNOT06), and 2007165 (TESTNOT03).

Figure 5B:
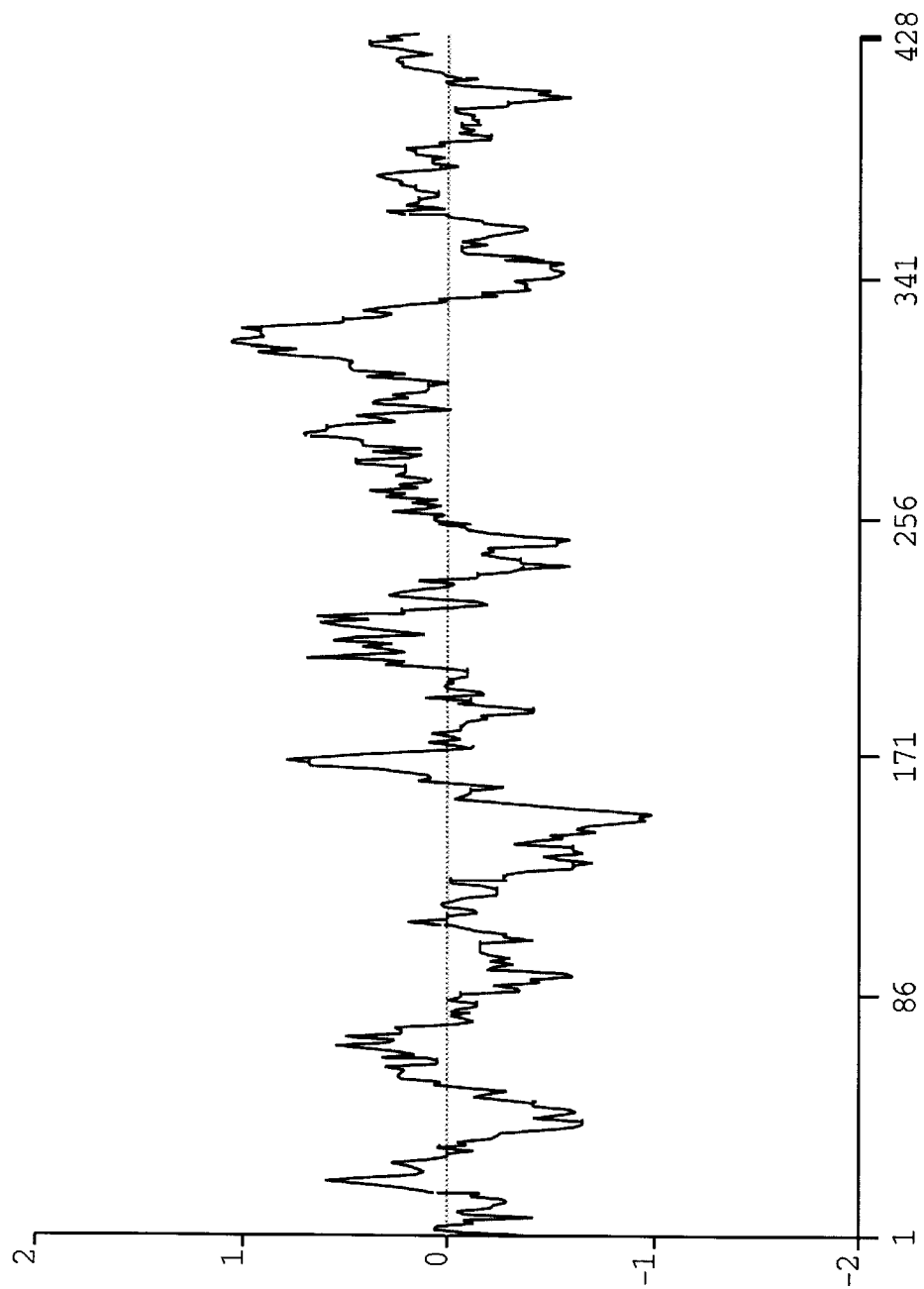

In one embodiment, the invention encompasses a polypeptide comprising the amino acid sequence of SEQ ID NO:1 as shown in FIGS. 1A, 1B, 1C, 1D, and 1E. HNDS-1 is 463 amino acids in length and has a potential signal peptide sequence at the N-terminus between approximately residues $M_1$ and $W_{37}$. The sequence contains several arginine and alanine residues characteristic of mitochondrial signal peptides and one arginine residue ($R_{35}$) is found near the potential cleavage site. A signature sequence of the 49 kDa subunit is found in the sequence $L_{116}$HRGTEKLIEYK. Cysteine residues representing potential intramolecular disulfide bridging sites are found at $C_{109}$, $C_{146}$, and $C_{347}$. Three N-linked glycosylation sites representing potential membrane anchor sites are found at $N_{79}$, $N_{250}$, and $N_{270}$. As shown in FIGS. 3A and 3B, HNDS-1 has chemical and structural homology with the 49 kDa subunit from cow (GI 833783; SEQ ID NO:5), and a similar protein from C. elegans (GI 470339; SEQ ID NO:6). In particular, HNDS-1 shares 96% and 66% identity with the bovine and C. elegans 49 kDa subunits, respectively. The 49 kDa signature sequence beginning at $L_{116}$ in HNDS-1 is conserved in the bovine 49 kDa subunit. The three cysteine residues and three potential N-linked glycosylation sites found in HNDS-1 are also conserved in the bovine subunit. HNDS-1 differs from the bovine and C. elegans subunits primarily by the presence of the potential mitochondrial signal peptide in HNDS-1 which may provide an additional or alternative means of targeting HNDS-1 to the mitochondrial membrane. As illustrated by FIGS. 5A and 5B, HNDS-1 and the bovine 49 kDa subunit have rather similar hydrophobicity plots. Northern analysis shows the expression of this sequence in various libraries, at least 41% of which are immortalized or cancerous, at least 26% of which involve smooth muscle tissues, and at least 16% of which involve inflammation and the immune response. Of particular note is the expression of HNDS-1 in cancers involving smooth muscle tissues, including stomach, colon, bladder, and lung.

Nucleic acids encoding HNDS-2 of the present invention were first identified in Incyte Clone 2072479 from the pancreatic islet cell cDNA library (ISLTNOT01) using a computer search for amino acid sequence alignments. A consensus sequence, SEQ ID NO:4, was derived from the following overlapping and/or extended nucleic acid sequences: Incyte Clones 608194 (COLNNOT01), 764228 (LUNGNOT04), 994267 (COLNNOT11), 1284509 (COLNNOT16), and 2072479 (ISLTNOT01).

Figure 6A:
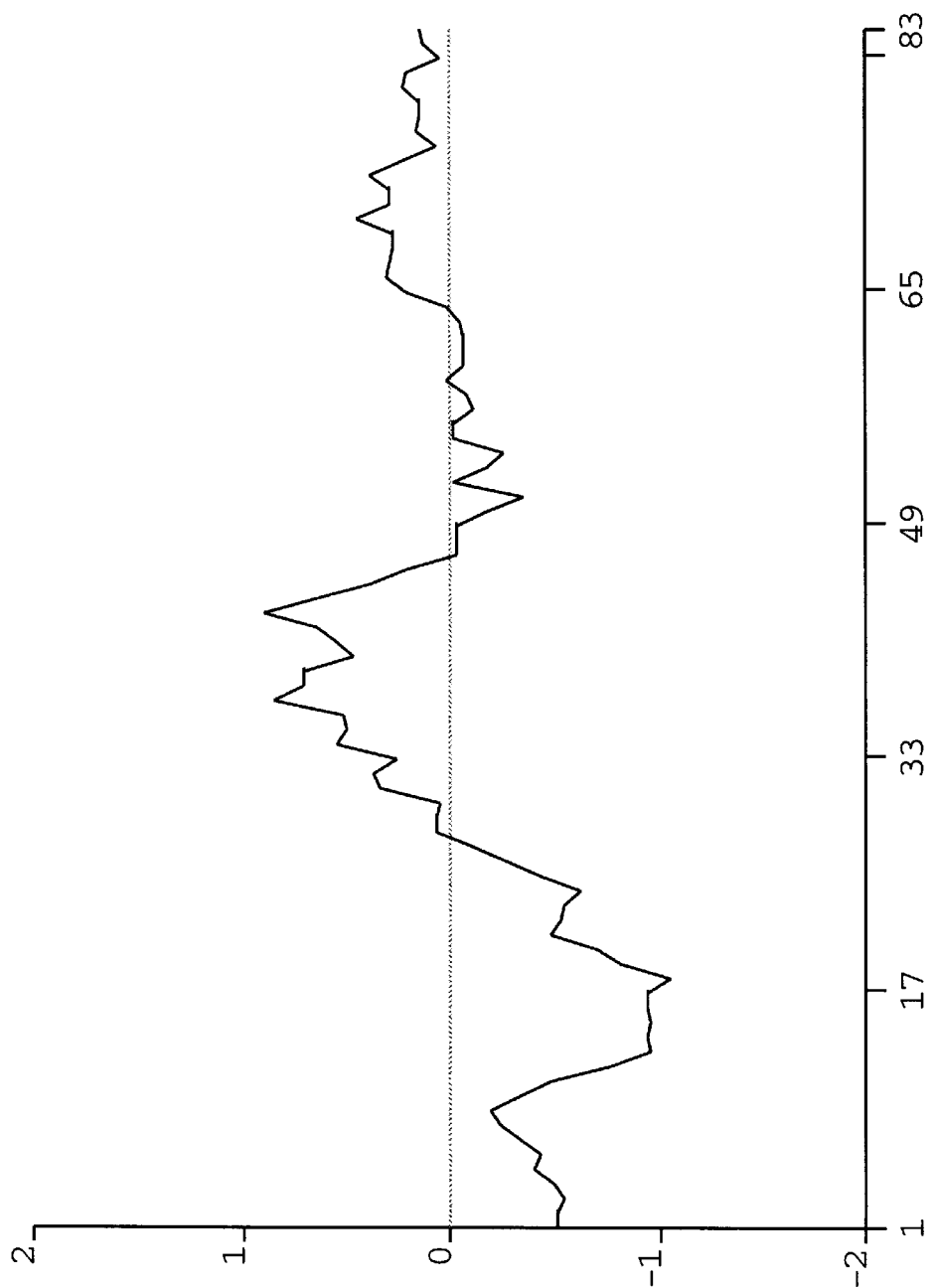
FIGS. 6A and 6B show the hydrophobicity plots for HNDS-2 (SEQ ID NO:3) and the bovine MLRQ subunit (SEQ ID NO:7), respectively; the positive X axis reflects amino acid position, and the negative Y axis, hydrophobicity (MACDNASIS PRO software).
Figure 6B:
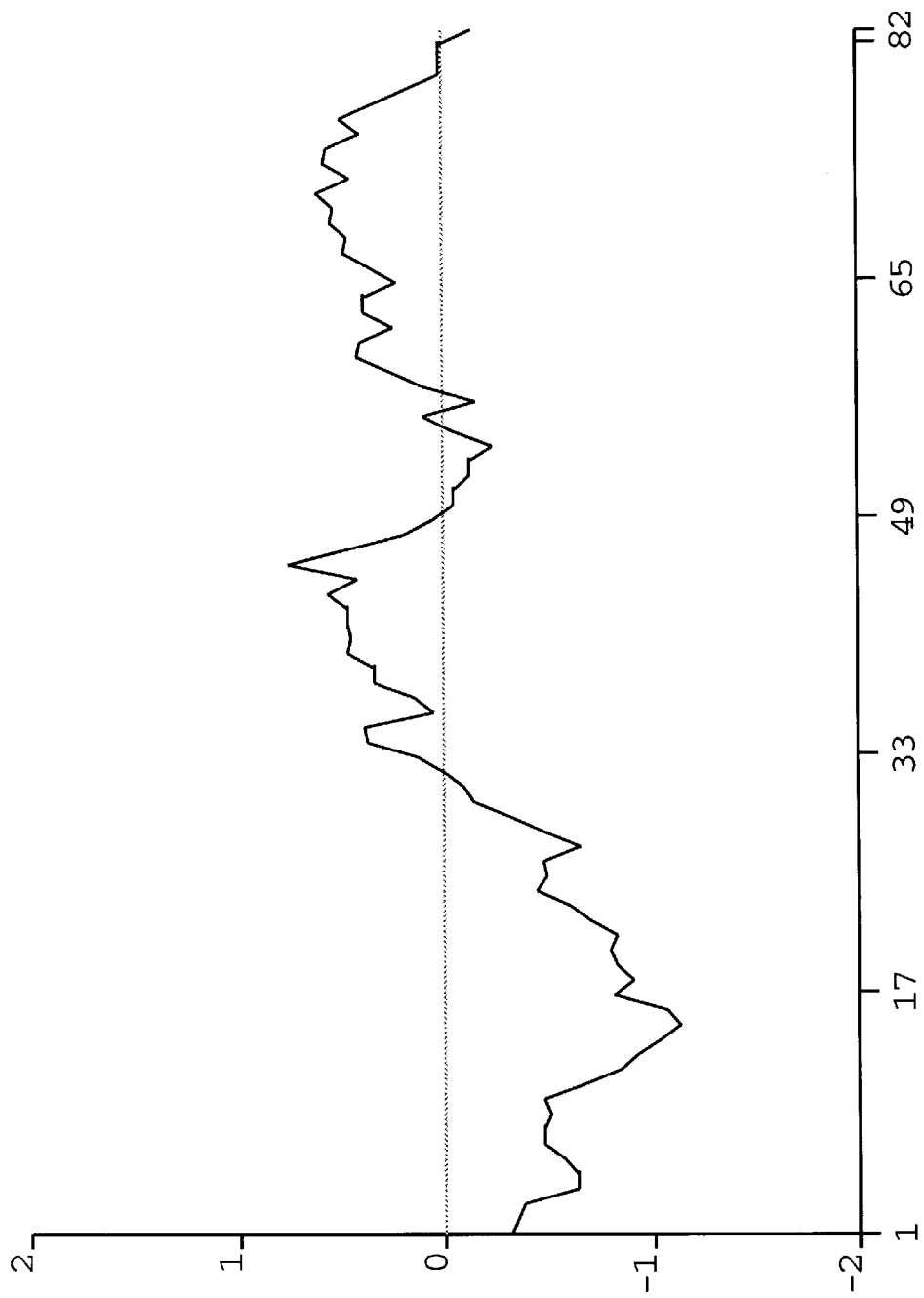

In another embodiment, the invention encompasses a polypeptide comprising the amino acid sequence of SEQ ID NO:3 as shown in FIGS. 2A and 2B. HNDS-2 is 83 amino acids in length and, as shown in FIG. 4, has chemical and structural homology with the bovine MLRQ subunit of NADH-D (GI 560; SEQ ID NO:7) and an MLRQ-like protein from mouse (GI 1401252; SEQ ID NO:8). In particular HNDS-3 shares 28% and 31% homology with the bovine and mouse MLRQ proteins, respectively. Like bovine MLRQ, HNDS-2 also contains a hydrophobic, N-terminal region of 25–30 amino acids with various hydrophobic residues including leucine, isoleucine, glycine, alanine and valine. The C-terminal half of the molecule is mostly hydrophilic with many charged residues including arginine, glutamic acid, lysine, and aspartic acid. Hydrophobicity plots illustrated in FIGS. 6A and 6B demonstrate the similarities in hydrophobic and hydrophilic regions between HNDS-2 and bovine MLRQ. Northern analysis shows the expression of HNDS-2 in various tissues, at least 43% of which are immortalized or cancerous, at least 55% of which are associated with smooth muscle tissue, and at least 33% of which involve inflammation or the immune response. Of particular note is the expression of HNDS-2 in inflammatory disease including Crohn's disease, ulcerative colitis, and lymphocytic thyroiditis.

The invention also encompasses HNDS variants. A preferred HNDS variant is one having at least 80%, and more preferably at least 90%, amino acid sequence identity to the HNDS amino acid sequence (SEQ ID NO:1 or SEQ ID NO:3) and which retains at least one biological, immunological or other functional characteristic or activity of HNDS. A most preferred HNDS variant is one having at least 95% amino acid sequence identity to SEQ ID NO:1 or SEQ ID NO:3.

The invention also encompasses polynucleotides which encode HNDS. Accordingly, any nucleic acid sequence which encodes the amino acid sequence of HNDS can be used to produce recombinant molecules which express HNDS. In a particular embodiment, the invention encompasses the polynucleotide comprising the nucleic acid sequence of SEQ ID NO:2 as shown in FIGS. 1A, 1B, 1C, 1D, and 1E. In another embodiment, the invention encompasses the polynucleotide comprising the nucleic acid sequence of SEQ ID NO:4 as shown in FIGS. 2A and 2B.

It will be appreciated by those skilled in the art that as a result of the degeneracy of the genetic code, a multitude of nucleotide sequences encoding HNDS, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HNDS, and all such variations are to be considered as being specifically disclosed.

Although nucleotide sequences which encode HNDS and its variants are preferably capable of hybridizing to the nucleotide sequence of the naturally occurring HNDS under appropriately selected conditions of stringency, it may be advantageous to produce nucleotide sequences encoding HNDS or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HNDS and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode HNDS and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HNDS or any fragment thereof.

Also encompassed by the invention are polynucleotide sequences that are capable of hybridizing to the claimed nucleotide sequences, and in particular, those shown in SEQ ID NO:2 or SEQ ID NO:4, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE DNA polymerase (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (Gibco/BRL, Galthersburg, Md.). Preferably, the process is automated with machines such as the Hamilton MICROLAB 2200 (Hamilton, Reno, Nev.), Peltier thermal cycler (PTC200; MJ Research, Watertown, Mass.) and the ABI CATALYST and 373 and 377 DNA sequencers (Perkin Elmer).

The nucleic acid sequences encoding HNDS may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR SOFTWARE, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HNDS may be used in recombinant DNA molecules to direct expression of HNDS, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HNDS.

As will be understood by those of skill in the art, it may be advantageous to produce HNDS-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HNDS encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HNDS may be ligated to a heterologous sequence to encode a fusion protein. For example, to screen peptide libraries for inhibitors of HNDS activity, it may be useful to encode a chimeric HNDS protein that can be recognized by a commercially available antibody. A fusion protein may also be engineered to contain a cleavage site located between the HNDS encoding sequence and the heterologous protein sequence, so that HNDS may be cleaved and purified away from the heterologous moiety.

In another embodiment, sequences encoding HNDS may be synthesized, in whole or in part, using chemical methods well known in the art (see Caruthers, M. H. et al. (1980) Nucl. Acids Res. Symp. Ser. 7:215–223, Horn, T. et al. (1980) Nucl. Acids Res. Symp. Ser. 7:225–232). Alternatively, the protein itself may be produced using chemical methods to synthesize the amino acid sequence of HNDS, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HNDS, or any part thereof, may be altered during direct synthesis and/or combined using chemical methods with sequences from other proteins, or any part thereof, to produce a variant polypeptide.

In order to express a biologically active HNDS, the nucleotide sequences encoding HNDS or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HNDS and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding HNDS. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HNDS, vectors based on SV40 or EBV may be used with an appropriate selectable marker.

In bacterial systems, a number of expression vectors may be selected depending upon the use intended for HNDS. For example, when large quantities of HNDS are needed for the induction of antibodies, vectors which direct high level expression of fusion proteins that are readily purified may be used. Such vectors include, but are not limited to, the multifunctional *E. coli* cloning and expression vectors such as the BLUESCRIPT phagemid (Stratagene), in which the sequence encoding HNDS may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HNDS may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HNDS. For example, in one such system, *Autographa californica* nuclear polyhedrosis virus (AcNPV) is used as a vector to express foreign genes in *Spodoptera frugiperda* cells or in Trichoplusia larvae. The sequences encoding HNDS may be cloned into a non-essential region of the virus, such as the polyhedrin gene, and placed under control of the polyhedrin promoter. Successful insertion of HNDS will render the polyhedrin gene inactive and produce recombinant virus lacking coat protein. The recombinant viruses may then be used to infect, for example, *S. frugiperda* cells or Trichoplusia larvae in which HNDS may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HNDS may be ligated into an adenovirus transcription/translation complex consisting of the late promoter and tripartite leader sequence. Insertion in a non-essential E1 or E3 region of the viral genome may be used to obtain a viable virus which is capable of expressing HNDS in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding HNDS. Such signals include the ATG initiation codon and adjacent sequences. In cases where sequences encoding HNDS, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express HNDS may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, Calif. et al. (1995) Methods Mol. Biol. 55:121–131).

Although the presence/absence of marker gene expression suggests that the gene of interest is also present, its presence and expression may need to be confirmed. For example, if the sequence encoding HNDS is inserted within a marker gene sequence, transformed cells containing sequences encoding HNDS can be identified by the absence of marker gene function. Alternatively, a marker gene can be placed in tandem with a sequence encoding HNDS under the control of a single promoter. Expression of the marker gene in response to induction or selection usually indicates expression of the tandem gene as well.

Alternatively, host cells which contain the nucleic acid sequence encoding HNDS and express HNDS may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding HNDS can be detected by DNA-DNA or DNA-RNA hybridization or amplification using probes or fragments or fragments of polynucleotides encoding HNDS. Nucleic acid amplification based assays involve the use of oligonucleotides or oligomers based on the sequences encoding HNDS to detect transformants containing DNA or RNA encoding HNDS.

A variety of protocols for detecting and measuring the expression of HNDS, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HNDS is preferred, but a competitive binding assay may be employed. These and other assays are described, among other places, in Hampton, R. et al. (1990*; Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HNDS include oligolabeling, nick translation, end-labeling or PCR amplification using a labeled nucleotide. Alternatively, the sequences encoding HNDS, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison, Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding HNDS may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HNDS may be designed to contain signal sequences which direct secretion of HNDS through a prokaryotic or eukaryotic cell membrane. Other constructions may be used to join sequences encoding HNDS to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGs extension/affinity purification system (Immunex Corp., Seattle, Wash.). The inclusion of cleavable linker sequences such as those specific for Factor XA or enterokinase (Invitrogen, San Diego, Calif.) between the purification domain and HNDS may be used to facilitate purification. One such expression vector provides for expression of a fusion protein containing HNDS and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3:263–281) while the enterokinase cleavage site provides a means for purifying HNDS from the fusion protein. A discussion of vectors which contain fusion proteins is provided in Kroll, D. J. et al. (1993; DNA Cell Biol. 12:441–453).

In addition to recombinant production, fragments of HNDS may be produced by direct peptide synthesis using solid-phase techniques (Merrifield J.) (1963) J. Am. Chem. Soc. 85:2149–2154). Protein synthesis may be performed using manual techniques or by automation. Automated synthesis may be achieved, for example, using Applied Biosystems 431 A peptide synthesizer (Perkin Elmer). Various fragments of HNDS may be chemically synthesized separately and combined using chemical methods to produce the full length molecule.

THERAPEUTICS

Chemical and structural homology exists among HNDS-1, the 49 kDa NADH-D subunit from cow (GI 833783), and a similar subunit from C. elegans (GI 470339). In addition, HNDS-1 is expressed in cancerous tissues, smooth muscle tissues, and in tissues associated with the immune response. Therefore, HNDS-1 appears to play a role in cancer, smooth muscle disorders, and immune disorders. In particular, increased expression or activity of HNDS-1 appears to be associated with cancer and immune disorders, while decreased expression or activity of HNDS-1 appears to be associated with smooth muscle disorders.

Therefore, in one embodiment, HNDS-1 or a fragment or derivative thereof may be administered to a subject to prevent or treat smooth muscle disorders. A smooth muscle disorder is defined as any impairment or alteration in the normal action of smooth muscle and may include, but is not limited to, angina, anaphylactic shock, arrhythmias, asthma, cardiovascular shock, Cushing's syndrome, hypertension, hypoglycemia, myocardial infarction, migraine, and pheochromocytoma, and myopathies including cardiomyopathy, encephalopathy, epilepsy, Kearns-Sayre syndrome, lactic acidosis, myoclonic disorder, and ophthalmoplegia. Smooth muscle includes, but is not limited to, that of the blood vessels, gastrointestinal tract, heart, and uterus.

In another embodiment, a vector capable of expressing HNDS-1, or a fragment or a derivative thereof, may also be administered to a subject to prevent or treat a smooth muscle disorder including, but not limited to, those described above.

In still another embodiment, an agonist which modulates the activity of HNDS-1 may also be administered to a subject to prevent or treat a smooth muscle disorder including, but not limited to, those described above.

In another embodiment, an antagonist of HNDS-1 may be administered to a subject to prevent or treat cancer. Cancers may include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HNDS-1 may be used directly as an antagonist or indirectly as a targeting or delivery mechanism for bringing a pharmaceutical agent to cells or tissue which express HNDS-1.

In another embodiment, a vector expressing the complement of the polynucleotide encoding HNDS-1 may be administered to a subject to treat or prevent cancer including, but not limited to, the types of cancer described above.

In another embodiment, an antagonist of HNDS-1 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding HNDS-1 may be administered to a subject to treat or prevent an immune disorder including, but not limited to, those described above.

Chemical and structural homology exists among HNDS-2, the bovine MLRQ subunit of NADH-D (GI 560) and the MLRQ-like protein from mouse (GI 1401252). In addition, HNDS-2 is expressed in cancerous tissues, smooth muscle tissues, and tissues associated with inflammation and the immune response. Therefore, HNDS-2 appears to play a role in cancer, smooth muscle disorders, and immune disorders. In particular, increased expression or activity of HNDS-2 appears to be associated with cancer and immune disorders, while decreased expression or activity of HNDS-2 appears to be associated with smooth muscle disorders.

Therefore, in one embodiment, HNDS-2 or a fragment or derivative thereof may be administered to a subject to prevent or treat smooth muscle disorders. Such disorders may include, but are not limited to, angina, anaphylactic shock, arrhythmias, asthma, cardiovascular shock, Cushing's syndrome, hypertension, hypoglycemia, myocardial infarction, migraine, and pheochromocytoma, and myopathies including cardiomyopathy, encephalopathy, epilepsy, Kearns-Sayre syndrome, lactic acidosis, myoclonic disorder, and ophthalmoplegia. Smooth muscle includes, but is not limited to, that of the blood vessels, gastrointestinal tract, heart, and uterus.

In another embodiment, a vector capable of expressing HNDS-2, or a fragment or a derivative thereof, may also be administered to a subject to prevent or treat a smooth muscle disorder including, but not limited to, those described above.

In still another embodiment, an agonist which modulates the activity of HNDS-2 may also be administered to a subject to prevent or treat a smooth muscle disorder including, but not limited to, those described above.

In another embodiment, an antagonist of HNDS-2 may be administered to a subject to prevent or treat cancer. Cancers may include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HNDS-2 may be used directly as an antagonist or indirectly as a targeting or delivery mechanism for bringing a pharmaceutical agent to cells or tissue which express HNDS-2.

In another embodiment, a vector expressing the complement of the polynucleotide encoding HNDS-2 may be administered to a subject to treat or prevent cancer including, but not limited to, the types of cancer described above.

In another embodiment, an antagonist of HNDS-2 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding HNDS-2 may be administered to a subject to treat or prevent an immune disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HNDS may be produced using methods which are generally known in the art. In particular, purified HNDS may be used to produce antibodies or to screen libraries of pharmaceutical agents to identify those which specifically bind HNDS.

Antibodies to HNDS may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HNDS or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, *BCG* (*bacilli Calmette-Guerin*) and *Corynebacterium parvum* are especially preferable.

It is preferred that the oligopeptides, peptides, or fragments used to induce antibodies to HNDS have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of HNDS amino acids may be fused with those of another protein such as keyhole limpet hemocyanin and antibody produced against the chimeric molecule.

Monoclonal antibodies to HNDS may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HNDS-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for HNDS may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HNDS and its specific antibody. A two-site, monoclonal-based immunoassay utilizing monoclonal antibodies reactive to two non-interfering HNDS epitopes is preferred, but a competitive binding assay may also be employed (Maddox, supra).

In another embodiment of the invention, the polynucleotides encoding HNDS, or any fragment or complement thereof, may be used for therapeutic purposes. In one aspect, the complement of the polynucleotide encoding HNDS may be used in situations in which it would be desirable to block the transcription of the mRNA. In particular, cells may be transformed with sequences complementary to polynucleotides encoding HNDS. Thus, complementary molecules or fragments may be used to modulate HNDS activity, or to achieve regulation of gene function. Such technology is now well known in the art, and sense or antisense oligonucleotides or larger fragments, can be designed from various locations along the coding or control regions of sequences encoding HNDS.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding HNDS. These techniques are described both in Sambrook et al. (supra) and in Ausubel et al. (supra).

Genes encoding HNDS can be turned off by transforming a cell or tissue with expression vectors which express high levels of a polynucleotide or fragment thereof which encodes HNDS. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding HNDS (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HNDS.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HNDS. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HNDS, antibodies to HNDS, mimetics, agonists, antagonists, or inhibitors of HNDS. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HNDS, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HNDS or fragments thereof, antibodies of HNDS, agonists, antagonists or inhibitors of HNDS, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HNDS may be used for the diagnosis of conditions or diseases characterized by expression of HNDS, or in assays to monitor patients being treated with HNDS, agonists, antagonists or inhibitors. The antibodies useful for diagnostic purposes may be prepared in the same manner as those described above for therapeutics. Diagnostic assays for HNDS include methods which utilize the antibody and a label to detect HNDS in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HNDS are known in the art and provide a basis for diagnosing altered or abnormal levels of HNDS expression. Normal or standard values for HNDS expression are established by combining body fluids or cell extracts taken from normal mammalian subjects, preferably human, with antibody to HNDS under conditions suitable for complex formation. The amount of standard complex formation may be quantified by various methods, but preferably by photometric, means. Quantities of HNDS expressed in control and disease samples from biopsied tissues are compared with the standard values. Deviation between standard and subject values establishes the parameters for diagnosing disease.

In another embodiment of the invention, the polynucleotides encoding HNDS may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HNDS may be correlated with disease. The diagnostic assay may be used to distinguish between absence, presence, and excess expression of HNDS, and to monitor regulation of HNDS levels during therapeutic intervention.

In one aspect, hybridization with PCR probes which are capable of detecting polynucleotide sequences, including genomic sequences, encoding HNDS or closely related molecules, may be used to identify nucleic acid sequences which encode HNDS. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HNDS, alleles, or related sequences.

Probes may also be used for the detection of related sequences, and should preferably contain at least 50% of the nucleotides from any of the HNDS encoding sequences. The hybridization probes of the subject invention may be DNA or RNA and derived from the nucleotide sequence of SEQ ID NO:2 or SEQ ID NO:4 or from genomic sequence including promoter, enhancer elements, and introns of the naturally occurring HNDS.

Means for producing specific hybridization probes for DNAs encoding HNDS include the cloning of nucleic acid sequences encoding HNDS or HNDS derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HNDS may be used for the diagnosis of conditions or disorders which are associated with expression of HNDS. Examples of such conditions or disorders include cancer such as adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; and smooth muscle disorders defined as any impairment or alteration in the normal action of smooth muscle including, but not limited to, angina, anaphylactic shock, arrhythmias, asthma, cardiovascular shock, Cushing's syndrome, hypertension, hypoglycemia, myocardial infarction, migraine, and pheochromocytoma, and myopathies including cardiomyopathy, encephalopathy, epilepsy, Kearns-Sayre syndrome, lactic acidosis, myoclonic disorder, and ophthalmoplegia. Smooth muscle includes, but is not limited to, that of the blood vessels, gastrointestinal tract, heart, and uterus. The polynucleotide sequences encoding HNDS may be used in Southern or northern analysis, dot blot, or other membrane-based technologies; in PCR technologies; or in dipstick, pin, ELISA assays or microarrays utilizing fluids or tissues from patient biopsies to detect altered HNDS expression. Such qualitative or quantitative methods are well known in the art.

In a particular aspect, the nucleotide sequences encoding HNDS may be useful in assays that detect activation or induction of various cancers, particularly those mentioned above. The nucleotide sequences encoding HNDS may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HNDS in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HNDS, a normal or standard profile for expression is established. This may be accomplished by combining body fluids or cell extracts taken from normal subjects, either animal or human, with a sequence, or a fragment thereof, which encodes HNDS, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HNDS may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HNDS include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Nati. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode HNDS may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding HNDS on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HNDS, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HNDS and the agent being tested, may be measured.

Another technique for drug screening which may be used provides for high throughput screening of compounds having suitable binding affinity to the protein of interest as described in published PCT application WO84/03564. In this method, as applied to HNDS large numbers of different small test compounds are synthesized on a solid substrate, such as plastic pins or some other surface. The test compounds are reacted with HNDS, or fragments thereof, and washed. Bound HNDS is then detected by methods well known in the art. Purified HNDS can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HNDS specifically compete with a test compound for binding HNDS. In this manner, the antibodies can be used to detect the presence of any peptide which shares one or more antigenic determinants with HNDS.

In additional embodiments, the nucleotide sequences which encode HNDS may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

THP1PLB01

The THP1PLB01 cDNA library was custom-constructed from activated human monocytes by Stratagene (Stratagene, La Jolla, Calif.). Poly(A+)RNA was purified from THP-1 cells which were cultured for 48 hr with 100 nm TPA and activated with 1 µg/ml LPS after 4 hr. cDNA synthesis was primed separately with both oligo d(T) and random hexamers and the two cDNA libraries were treated separately. Synthetic adaptor oligonucleotides were ligated onto cDNA ends enabling insertion into UNI-ZAP vector system (Stratagene). Finally, the two libraries were combined into a single library by mixing equal numbers of bacteriophage.

The cDNA library can be screened with either DNA probes or antibody probes and the BLUESCRIPT phagemid (Stratagene) can be rapidly excised in vivo. The custom-constructed library phage particles were transfected into *E. coli* host strain XLI-BLUE competent cells (Stratagene). Alternative unidirectional vectors include but are not limited to pcDNAI (Invitrogen, San Diego, Calif.) and pSHlox-1 (Novagen, Madison, Wis.).

ISLTNOT01

The ISLTNOT01 cDNA library was constructed from total RNA isolated from microscopically normal pancreatic islet cells (specimen #A143, Pfizer, Inc., New York, N.Y.). The mRNA was then isolated using the OLIGOTEX kit (QIAGEN, Inc.; Chatsworth, Calif.) and used to construct the cDNA library.

The mRNA was handled according to the recommended protocols in the SUPERSCRIPT cDNA systhesis and plasmid cloning kit (Cat. #18248-013; Gibco/BRL). cDNAs were fractionated on a SEPHAROSE CL4B column (Cat. #275105-01; Pharmacia), and those cDNAs exceeding 400 bp were ligated into pINCY. The plasmid pSport I was subsequently transformed into DH5a competent cells (Cat. #18258-012; Gibco/BRL).

II Isolation and Sequencing of cDNA Clones

THP1PLB01

The phagemid forms of individual cDNA clones were obtained by the in vivo excision process, in which the host bacterial strain was coinfected with both the lambda library phage and an f1 helper phage. Polypeptides derived from both the library-containing phage and the helper phage nicked the lambda DNA, initiated new DNA synthesis from defined sequences on the lambda target DNA and created a smaller, single stranded circular phagemid DNA molecule that included all DNA sequences of the BLUESCRIPT phagemid and the cDNA insert.

The phagemid DNA was secreted from the cells, purified, and used to re-infect fresh host cells, where the double stranded phagemid DNA was produced. Because the phagemid carries the gene for β-lactamase, the newly-transformed bacteria are selected on medium containing ampicillin.

Phagemid DNA was purified using the MAGIC MINI-PREPS DNA purification system (Promega catalogue #A7100; Promega, Madison, Wis.). The DNA was eluted from the purification resin already prepared for DNA sequencing and other analytical manipulations. Phagemid DNA was also purified using the QIAWELL-8 plasmid QIAWELL PLUS, and QIAWELL ULTRA DNA purification system (QIAGEN, Chatsworth, Calif.). The DNA was eluted from the purification resin already prepared for DNA sequencing and other analytical manipulations.

The cDNA inserts from random isolates were sequenced in part. Conventional enzymatic methods employ DNA polymerase Klenow fragment, SEQUENASE DNA polymerase or Taq polymerase to extend DNA chains from an oligonucleotide primer annealed to the DNA template of interest. Methods have been developed for the use of both single- and double stranded templates. The chain termination reaction products are usually electrophoresed on urea-acrylamide gels and are detected either by autoradiography (for radionuclide-labelled precursors) or by fluorescence (for fluorescent labeled precursors). Recent improvements in mechanized reaction preparation, sequencing and analysis using the fluorescent detection method have permitted expansion in the number of sequences that can be determined per day (such as the Applied Biosystems 373 DNA sequencer and CATALYST 800).

ISLTNOT01

Plasmid DNA was released from the cells and purified using the REAL PREP96-well plasmid kit (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton MICROLAB2200 (Hamilton, Reno, Nev.) in combination with Peltier thermal cyclers (PTC200 from MJ Research, Watertown, Mass.) and Applied Biosystems 377 DNA sequencing systems; and the reading frame was determined.

III Homology Searching of cDNA Clones and Their Deduced Proteins

THP1PBL01

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1 990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.
ISLTNOT01

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, which stands for Basic Local Alignment Search Tool (Altschul, S. F. (1993) J. Mol. Evol 36:290–300; Altschul, et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J. Mol. Evol. 36:290–300; Altschul, S. F. et al. (1990) J. Mol. Evol. 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

% sequence identity×% maximum BLAST score/100

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HNDS occurs. Abundance and percent abundance are also reported. Abundance directly reflects the number of times a particular transcript is represented in a cDNA library, and percent abundance is abundance divided by the total number of sequences examined in the cDNA library.

V Extension of HNDS Encoding Polynucleotides

The nucleic acid sequence of the Incyte Clones 13075 and 2072479 were used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 primer analysis software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cyclers (PTC200; M. J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min Step 11 Repeat step 8–10 for 12 cycles Step 12 72° C. for 8 min Step 13 4° C. (and holding)

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK DNA gel purification kit (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 µl of liquid LB/2× Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 nits of rTth DNA polymerase, a vector primer, and one or both of the gene specific primers used for the extension reaction were added to each well. Amplification was performed using the following conditions:

Step 1 94° C. for 60 sec

Step 2 94° C. for 20 sec

Step 3 55° C. for 30 sec

Step 4 72° C. for 90 sec

Step 5 Repeat steps 2–4 for an additional 29 cycles

Step 6 72° C. for 180 sec

Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 or SEQ ID NO:4 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 or SEQ ID NO:4 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 primer analysis software (National Biosciences), labeled by combining 50 pmol of each oligomer and 250 µCi of [$\gamma$-$^{32}$P] adenosine triphosphate (Amersham) and T4 polynucleotide kinase (DuPont NEN®, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bg1II, Eco RI, Pst I, Xba 1, or Pvu II; DuPont NEN®).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR autoradiography film (Kodak, Rochester, N.Y.) is exposed to the blots, or the blots are placed in a PHOSPHOIMAGER cassette (Molecular Dynamics, Sunnyvale, Calif.) for several hours, hybridization patterns are compared visually.

VII Microarrays

To produce oligonucleotides for a microarray, one of the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. 0 This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the HNDS-encoding sequence, or any part thereof, is used to decrease or inhibit expression of naturally occurring HNDS. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of HNDS, SEQ ID NO:1 or SEQ ID NO:3. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HNDS-encoding transcript.

IX Expression of HNDS

Expression of HNDS is accomplished by subcloning the cDNAs into appropriate vectors and transforming the vectors into host cells. In this case, the cloning vector is also used to express HNDS in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HNDS into the bacterial growth media which can be used directly in the following assay for activity.

X Demonstration of HNDS Activity

HNDS activity is measured in the reconstituted NADH-D complex by the catalysis of electron transfer from NADH to decylubiquinone (DB). The reaction contains 10 μg/mL NADH-D protein, 20 μM NADH in 50 mM TRIS-HCL buffer, pH 7.5, 50 mM NaCl, and 1 mM KCN. The reaction is started by addition of DB at 2 uM and followed by the change in absorbance at 340 nm due to the oxidation of NADH using an ultraviolet spectrophotometer. NADH-D complex reconstituted in the absence of HNDS is compared as a negative control. The activity of HNDS in the reconstituted NADH-D complex is proportional to the rate of change of absorbance at 340 nm.

XI Production of HNDS Specific Antibodies

HNDS that is substantially purified using PAGE electrophoresis (Sambrook, supra), or other purification techniques, is used to immunize rabbits and to produce antibodies using standard protocols. The amino acid sequence deduced from SEQ ID NO:2 or SEQ ID NO:4 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems peptide synthesizer model 431 A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring HNDS Using Specific Antibodies

Naturally occurring or recombinant HNDS is substantially purified by immunoaffinity chromatography using antibodies specific for HNDS. An immunoaffinity column is constructed by covalently coupling HNDS antibody to an activated chromatographic resin, such as CnBr-activated SEPHAROSE (Pharmacia & Upjohn). After the coupling, the resin is blocked and washed according to the manufacturer's instructions.

Media containing HNDS is passed over the immunoaffinity column, and the column is washed under conditions that allow the preferential absorbance of HNDS (e.g., high ionic strength buffers in the presence of detergent). The column is eluted under conditions that disrupt antibody/HNDS binding (eg, a buffer of pH 2–3 or a high concentration of a chaotrope, such as urea or thiocyanate ion), and HNDS is collected.

XIII Identification of Molecules Which Interact with HNDS

HNDS or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HNDS, washed and any wells with labeled HNDS complex are assayed. Data obtained using different concentrations of HNDS are used to calculate values for the number, affinity, and association of HNDS with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding the NADH dehydrogenase subunit having the amino acid sequence of SEQ ID NO:1.

2. A composition comprising the polynucleotide sequence of claim 1.

3. A polynucleotide which is fully complementary to the polynucleotide of claim 1.

4. An isolated and purified polynucleotide having the sequence of SEQ ID NO:2.

5. A polynucleotide which is fully complementary to the polynucleotide of claim 4.

6. An isolated and purified polynucleotide encoding the NADH dehydrogenase subunit having the amino acid sequence of SEQ ID NO:3.

7. A composition comprising the polynucleotide sequence of claim 6.

8. A polynucleotide which is fully complementary to the polynucleotide of claim 6.

9. An isolated and purified polynucleotide having the sequence of SEQ ID NO:4.

10. A polynucleotide which is fully complementary to the polynucleotide of claim 9.

11. An expression vector containing the polynucleotide of claim 1.

12. An expression vector containing the polynucleotide of claim 6.

13. A host cell containing the vector of claim 11.

14. A host cell containing the vector of claim 12.

15. A method for producing a polypeptide having the amino acid sequence of SEQ ID NO:1, the method comprising the steps of:
   a) culturing the host cell of claim 13 under conditions suitable for the expression of the polypeptide; and
   b) recovering the polypeptide from the host cell culture.

16. A method for producing a polypeptide having the amino acid sequence of SEQ ID NO:3, the method comprising the steps of:
   a) culturing the host cell of claim 14 under conditions suitable for the expression of the polypeptide; and
   b) recovering the polypeptide from the host cell culture.

17. A method for detecting a polynucleotide which encodes NADH dehydrogenase subunit in a biological sample comprising the steps of:
   a) hybridizing the polynucleotide of claim 3 to nucleic acid material of a biological sample, thereby forming a hybridization complex; and
   b) detecting said hybridization complex, wherein the presence of said complex correlates with the presence of a polynucleotide encoding NADH dehydrogenase subunit in said biological sample.

18. The method of claim 17 wherein the nucleic acid material is amplified by the polymerase chain reaction prior to hybridization.

19. A method for detecting a polynucleotide which encodes NADH dehydrogenase subunit in a biological sample comprising the steps of:
   a) hybridizing the polynucleotide of claim 8 to nucleic acid material of a biological sample, thereby forming a hybridization complex; and
   b) detecting said hybridization complex, wherein the presence of said complex correlates with the presence of a polynucleotide encoding NADH dehydrogenase subunit in said biological sample.

20. The method of claim 19 wherein the nucleic acid material is amplified by the polymerase chain reaction prior to hybridization.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
(A) LENGTH: 463 amino acids (B) TYPE: amino acid
(C) STRANDEDNESS: single
(D) TOPOLOGY: linear (vii) IMMEDIATE SOURCE:
(A) LIBRARY: THPIPLB01
(B) CLONE: 013075

(xi) SEQUENCE DESCRIPTION: SEQ ID NO:1:

```
Met Ala Ala Leu Arg Ala Leu Cys Gly Phe Arg Gly Val Ala Ala Gln
 1               5                  10                  15

Val Leu Arg Pro Gly Ala Gly Val Arg Leu Pro Ile Gln Pro Ser Arg
            20                  25                  30

Gly Val Arg Gln Trp Gln Pro Asp Val Glu Trp Ala Gln Gln Phe Gly
        35                  40                  45

Gly Ala Val Met Tyr Pro Ser Lys Glu Thr Ala His Trp Lys Pro Pro
50                  55                  60

Pro Trp Asn Asp Val Asp Pro Lys Asp Thr Ile Val Lys Asn Ile
65                  70                  75                  80

Thr Leu Asn Phe Gly Pro Gln His Pro Ala Ala His Gly Val Leu Arg
                85                  90                  95

Leu Val Met Glu Leu Ser Gly Glu Met Val Arg Lys Cys Asp Pro His
            100                 105                 110

Ile Gly Leu Leu His Arg Gly Thr Glu Lys Leu Ile Glu Tyr Lys Thr
        115                 120                 125

Tyr Leu Gln Ala Leu Pro Tyr Phe Asp Arg Leu Asp Tyr Val Ser Met
130                 135                 140

Met Cys Asn Glu Gln Ala Tyr Ser Leu Ala Val Glu Lys Leu Leu Asn
145                 150                 155                 160

Ile Arg Pro Pro Pro Arg Ala Gln Trp Ile Arg Val Leu Phe Gly Glu
                165                 170                 175

Ile Thr Arg Leu Leu Asn His Ile Met Ala Val Thr Thr His Ala Leu
            180                 185                 190

Asp Leu Gly Ala Met Thr Pro Phe Phe Trp Leu Phe Glu Glu Arg Glu
        195                 200                 205

Lys Met Phe Glu Phe Tyr Glu Arg Val Ser Gly Ala Arg Met His Ala
210                 215                 220

Ala Tyr Ile Arg Pro Gly Gly Val His Gln Asp Leu Pro Leu Gly Leu
225                 230                 235                 240

Met Asp Asp Ile Tyr Gln Phe Ser Lys Asn Phe Ser Leu Arg Leu Asp
                245                 250                 255

Glu Leu Glu Glu Leu Leu Thr Asn Asn Arg Ile Trp Arg Asn Arg Thr
            260                 265                 270

Ile Asp Ile Gly Val Val Thr Ala Glu Glu Ala Leu Asn Tyr Gly Phe
        275                 280                 285

Ser Gly Val Met Leu Arg Gly Ser Gly Ile Gln Trp Asp Leu Arg Lys
290                 295                 300

Thr Gln Pro Tyr Asp Val Tyr Asp Gln Val Glu Phe Asp Val Pro Val
305                 310                 315                 320

Gly Ser Arg Gly Asp Cys Tyr Asp Arg Tyr Leu Cys Arg Val Glu Glu
                325                 330                 335

Met Arg Gln Ser Leu Arg Ile Ile Ala Gln Cys Leu Asn Lys Met Pro
            340                 345                 350

Pro Gly Glu Ile Lys Val Asp Asp Ala Lys Val Ser Pro Pro Lys Arg
        355                 360                 365

Ala Glu Met Lys Thr Ser Met Glu Ser Leu Ile His His Phe Lys Leu
```

```
               370                375                380
Tyr Thr Glu Gly Tyr Gln Val Pro Pro Gly Ala Thr Tyr Thr Ala Ile
385                390                395                400

Glu Ala Pro Lys Gly Glu Phe Gly Val Tyr Leu Val Ser Asp Gly Ser
                405                410                415

Ser Arg Pro Tyr Arg Cys Lys Ile Lys Ala Pro Gly Phe Ala His Leu
            420                425                430

Ala Gly Leu Asp Lys Met Ser Lys Gly His Met Leu Ala Asp Val Val
        435                440                445

Ala Ile Ile Gly Thr Gln Asp Ile Val Phe Gly Glu Val Asp Arg
    450                455                460
```

(2) INFORMATION FOR SEQ ID NO:2:

(i) SEQUENCE CHARACTERISTICS:
        (A) LENGTH: 1560 base pairs
        (B) TYPE: nucleic acid
        (C) STRANDEDNESS: single
        (D) TOPOLOGY: linear (vii) IMMEDIATE SOURCE:
        (A) LIBRARY: THPIPLB01
        (B) CLONE: 013075

(xi) SEQUENCE DESCRIPTION: SEQ ID NO:2:

```
AGATGGCGGC GCTGAGGGCT TTGTGCGGCT TCCGGGCGT CGCGGCCCAG GTGCTGCGGC    60

CTGGGGCTGG AGTCCGATTG CCGATTCAGC CCAGCAGAGG TGTTCGGCAG TGGCAGCCAG   120

ATGTGGAATG GCACAGCAG TTTGGGGGAG CTGTTATGTA CCCAAGCAAA GAAACAGCCC   180

ACTGGAAGCC TCCACCTTGG AATGATGTGG ACCCTCCAAA GGACACAATT GTGAAGAACA   240

TTACCCTGAA CTTTGGGCCC CAACACCCAG CAGCGCATGG TGTCCTGCGA CTAGTGATGG   300

AATTGAGTGG GGAGATGGTG CGGAAGTGTG ATCCTCACAT CGGGCTCCTG CACCGAGGCA   360

CTGAGAAGCT CATTGAATAC AAGACCTATC TTCAGGCCCT TCCATACTTT GACCGGCTAG   420

ACTATGTGTC CATGATGTGT AACGAACAGG CCTATTCTCT AGCTGTGGAG AAGTTGCTAA   480

ACATCCGGCC TCCTCCTCGG GCACAGTGGA TCCGAGTGCT GTTTGGAGAA ATCACACGTT   540

TGTTGAACCA CATCATGGCT GTGACCACAC ATGCCCTGGA CCTTGGGGCC ATGACCCCTT   600

TCTTCTGGCT GTTTGAAGAA AGGGAGAAGA TGTTTGAGTT CTACGAGCGA GTGTCTGGAG   660

CCCGAATGCA TGCTGCTTAT ATCCGGCCAG GAGGAGTGCA CCAGGACCTA CCCCTTGGGC   720

TTATGGATGA CATTTATCAG TTTTCTAAGA ACTTCTCTCT TCGGCTTGAT GAGTTGGAGG   780

AGTTGCTGAC CAACAATAGG ATCTGGCGAA ATCGGACAAT TGACATTGGG GTTGTAACAG   840

CAGAAGAAGC ACTTAACTAT GGTTTTAGTG GAGTGATGCT TCGGGGCTCA GGCATCCAGT   900

GGGACCTGCG GAAGACCCAG CCCTATGATG TTTACGACCA GGTTGAGTTT GATGTTCCTG   960

TTGGTTCTCG AGGGGACTGC TATGATAGGT ACCTGTGCCG GGTGGAGGAG ATGCGCCAGT  1020

CCCTGAGAAT TATCGCACAG TGTCTAAACA AGATGCCTCC TGGGGAGATC AAGGTTGATG  1080

ATGCCAAAGT GTCTCCACCT AAGCGAGCAG AGATGAAGAC TTCCATGGAG TCACTGATTC  1140

ATCACTTTAA GTTGTATACT GAGGGCTACC AAGTTCCTCC AGGAGCCACA TATACTGCCA  1200

TTGAGGCTCC CAAGGGAGAG TTTGGGGTGT ACCTGGTGTC TGATGGCAGC AGCCGCCCTT  1260

ATCGATGCAA GATCAAGGCT CCTGGTTTTG CCCATCTGGC TGGTTTGGAC AAGATGTCTA  1320

AGGGACACAT GTTGGCAGAT GTCGTTGCCA TCATAGGTAC CCAAGATATT GTATTTGGAG  1380

AAGTAGATCG GTGAGCAGGG GAGCAGCGTT TGATCCCCCC TGCCTATCAG CTTCTTCTGT  1440
```

```
GGAGCCTGTT CCTCACTGGA AATTGGCCTC TGTGTGTGTG TGTGTGTGTG TGTGTGTGTG      1500

TGTGTGTATG TTCATGTACA CTTGGCTGTC AGGCTTTCTG TGCATGTACT AAAAAAAAAA      1560
```

(2) INFORMATION FOR SEQ ID NO:3:

(i) SEQUENCE CHARACTERISTICS:
        (A) LENGTH: 83 amino acids
        (B) TYPE: amino acid
        (C) STRANDEDNESS: single
        (D) TOPOLOGY: linear (vii) IMMEDIATE SOURCE:
        (A) LIBRARY: ISLTNOT01
        (B) CLONE: 2072479

(xi) SEQUENCE DESCRIPTION: SEQ ID NO:3:

```
Met Ser Phe Phe Gln Leu Leu Met Lys Arg Lys Glu Leu Ile Pro Leu
 1               5                  10                  15

Val Val Phe Met Thr Val Ala Ala Gly Gly Ala Ser Ser Phe Ala Val
                20                  25                  30

Tyr Ser Leu Trp Lys Thr Asp Val Ile Leu Asp Arg Lys Lys Asn Pro
            35                  40                  45

Glu Pro Trp Glu Thr Val Asp Pro Thr Val Pro Gln Lys Leu Ile Thr
50                  55                  60

Ile Asn Gln Gln Trp Lys Pro Ile Glu Glu Leu Gln Asn Val Gln Arg
65                  70                  75                  80

Val Thr Lys
```

(2) INFORMATION FOR SEQ ID NO:4:

(i) SEQUENCE CHARACTERISTICS:
        (A) LENGTH: 570 base pairs
        (B) TYPE: nucleic acid
        (C) STRANDEDNESS: single
        (D) TOPOLOGY: linear (vii) IMMEDIATE SOURCE:
        (A) LIBRARY: ISLTNOT01
        (B) CLONE: 2072479

(xi) SEQUENCE DESCRIPTION: SEQ ID NO:4:

```
CGCTGGCCCG GCCCACCCGG GGCGGTTGTG GTCGCTATAT ATAAGGTGGG GAGGCCGCCG       60

GCCCGTTCGG TTCCGGGCGT TACCATCGTC CGTGCGCACC GCCCGGCGTC CAGATTTGGC      120

AATTCTTCGC TGAAGTCATC ATGAGCTTTT TCCAACTCCT GATGAAAAGG AAGGAACTCA      180

TTCCCTTGGT GGTGTTCATG ACTGTGGCGG CGGGTGGAGC CTCATCTTTC GCTGTGTATT      240

CTCTTTGGAA AACCGATGTG ATCCTTGATC GAAAAAAAA TCCAGAACCT TGGGAAACTG       300

TGGACCCTAC TGTACCTCAA AAGCTTATAA CAATCAACCA ACAATGGAAA CCCATTGAAG      360

AGTTGCAAAA TGTCCAAAGG GTGACCAAAT GACGAGCCCT CGCCTCTTTC TTCTGAAGAG      420

TACTCTATAA ATCTAGTGGA AACATTTCTG CACAAACTAG ATTCTGGACA CCAGTGTGCG      480

GAAATGCTTC TGCTACATTT TTAGGGTTTG TCTACATTTT TTGGGCTCTG GATAAGGAAT      540

TAAAGGAGTG CAGCAATAAC TGCACTGTCT                                       570
```

(2) INFORMATION FOR SEQ ID NO:5:

(i) SEQUENCE CHARACTERISTICS:
        (A) LENGTH: 428 amino acids
        (B) TYPE: amino acid
        (C) STRANDEDNESS: single
        (D) TOPOLOGY: linear (vii) IMMEDIATE SOURCE:
    (A) LIBRARY: GenBank
    (B) CLONE: 833783

(xi) SEQUENCE DESCRIPTION: SEQ ID NO:5:

```
Gln Trp Gln Pro Asp Val Glu Trp Ala Glu Gln Tyr Gly Gly Ala Val
 1               5                  10                  15

Met Tyr Pro Thr Lys Glu Thr Ala His Trp Lys Pro Pro Trp Asn
            20                  25                  30

Asp Val Asp Pro Pro Lys Asp Thr Leu Val Ser Asn Leu Thr Leu Asn
            35                  40                  45

Phe Gly Pro Gln His Pro Ala Ala His Gly Val Leu Arg Leu Val Met
 50                  55                  60

Glu Leu Ser Gly Glu Met Val Arg Lys Cys Asp Pro His Ile Gly Leu
 65                  70                  75                  80

Leu His Arg Gly Thr Glu Lys Leu Ile Glu Tyr Lys Thr Tyr Leu Gln
                    85                  90                  95

Ala Leu Pro Tyr Phe Asp Arg Leu Asp Tyr Val Ser Met Met Cys Asn
                100                 105                 110

Glu Gln Ala Tyr Ser Leu Ala Val Glu Lys Leu Leu Asn Ile Arg Pro
                115                 120                 125

Pro Pro Arg Ala Gln Trp Ile Arg Val Leu Phe Gly Glu Ile Thr Arg
130                 135                 140

Leu Leu Asn His Ile Met Ala Val Thr Thr His Ala Leu Asp Ile Gly
145                 150                 155                 160

Ala Met Thr Pro Phe Phe Trp Met Phe Glu Glu Arg Glu Lys Met Phe
                165                 170                 175

Glu Phe Tyr Glu Arg Val Ser Gly Ala Arg Met His Ala Ala Tyr Val
                180                 185                 190

Arg Pro Gly Gly Val His Gln Asp Leu Pro Leu Gly Leu Met Asp Asp
                195                 200                 205

Ile Tyr Glu Phe Ser Lys Asn Phe Ser Leu Arg Ile Asp Glu Leu Glu
                210                 215                 220

Glu Met Leu Thr Asn Asn Arg Ile Trp Arg Asn Arg Thr Val Asp Ile
225                 230                 235                 240

Gly Ile Val Thr Ala Glu Asp Ala Leu Asn Tyr Gly Phe Ser Gly Val
                245                 250                 255

Met Leu Arg Gly Ser Gly Ile Gln Trp Asp Leu Arg Lys Thr Gln Pro
                260                 265                 270

Tyr Asp Val Tyr Asp Gln Val Glu Phe Asp Val Pro Ile Gly Ser Arg
                275                 280                 285

Gly Asp Cys Tyr Asp Arg Tyr Leu Cys Arg Val Glu Glu Met Arg Gln
290                 295                 300

Ser Ile Arg Ile Ile Ser Gln Cys Leu Asn Lys Met Pro Pro Gly Glu
305                 310                 315                 320

Ile Lys Val Asp Asp Ala Lys Val Ser Pro Pro Lys Arg Ala Glu Met
                325                 330                 335

Lys Thr Ser Met Glu Ser Leu Ile His His Phe Lys Leu Tyr Thr Glu
                340                 345                 350

Gly Tyr Gln Val Pro Pro Gly Ala Thr Tyr Thr Ala Ile Glu Ala Pro
                355                 360                 365

Lys Gly Glu Phe Gly Val Tyr Leu Val Ser Asp Gly Ser Ser Arg Pro
                370                 375                 380

Tyr Arg Cys Lys Ile Lys Ala Pro Gly Phe Ala His Leu Ala Gly Leu
385                 390                 395                 400
```

```
Asp Lys Met Ser Lys Gly His Met Leu Ala Asp Val Val Ala Ile Ile
                405                 410                 415
Gly Thr Gln Asp Ile Val Phe Gly Glu Val Asp Arg
            420                 425

(2) INFORMATION FOR SEQ ID NO:6:

(i) SEQUENCE CHARACTERISTICS:
        (A) LENGTH: 474 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 470339

(xi) SEQUENCE DESCRIPTION: SEQ ID NO:6:

Met Leu Ser Arg Ser Leu His Pro Leu Arg Ala Val Ala Cys Ala Arg
 1               5                  10                  15
Pro Ala Ile Ser Asn Arg Asp Ser His Thr Ile Trp Tyr Pro Asp Ala
             20                  25                  30
Lys Phe Glu Arg Gln Phe Lys Thr Gly Gly Thr Leu Gly Lys Leu Trp
         35                  40                  45
Met Ser Glu Arg Val Ser Asp Phe Asp Asp Gln Ile Gly Leu Asp Lys
 50                  55                  60
Leu Glu Lys Leu Ala Tyr Ser Asp Pro Val Leu Ser Asp Asn Tyr Glu
65                  70                  75                  80
Gly Lys Lys Arg Glu Lys Asn Leu Glu Asn Met Ile Leu Asn Phe Gly
                 85                  90                  95
Pro Gln His Pro Ala Ala His Gly Val Leu Arg Leu Val Leu Lys Leu
            100                 105                 110
Glu Gly Glu Val Ile Ile Lys Ala Ile Pro His Ile Gly Leu Leu His
        115                 120                 125
Arg Ala Thr Glu Lys Leu Ile Glu His Lys Thr Tyr Thr Gln Ala Leu
130                 135                 140
Pro Tyr Phe Asp Arg Leu Asp Tyr Val Ser Met Met Cys Asn Glu Gln
145                 150                 155                 160
Ala Phe Ser Leu Ala Ile Glu Lys Leu Leu Gly Ile Asp Val Pro Pro
                165                 170                 175
Arg Ala Lys Tyr Ile Arg Ile Leu Phe Gly Glu Leu Thr Arg Ile Gln
            180                 185                 190
Asn His Ile Met Gly Ile Thr Thr His Ala Leu Asp Val Gly Ala Met
        195                 200                 205
Thr Pro Phe Phe Trp Met Phe Glu Glu Arg Glu Lys Leu Phe Glu Phe
210                 215                 220
Ser Glu Arg Val Ser Gly Ala Arg Met His Ala Asn Tyr Val Arg Pro
225                 230                 235                 240
Gly Gly Val Ala Trp Asp Leu Pro Val Gly Leu Met Asp Asp Ile Tyr
                245                 250                 255
Asp Trp Ala Val Lys Phe Pro Ala Arg Ile Asp Glu Leu Glu Asp Met
            260                 265                 270
Leu Thr Glu Asn Arg Ile Trp Lys Ala Arg Thr Val Asp Ile Gly Leu
        275                 280                 285
Val Ser Ala Ser Asp Ala Leu Asn Trp Gly Phe Ser Gly Val Met Val
290                 295                 300
Arg Gly Ser Gly Ile Lys Gln Asp Val Arg Lys Thr Glu Pro Tyr Asp
```

```
        305                 310                 315                 320
    Ala Tyr Ala Asp Met Glu Phe Asp Val Pro Ile Gly Thr Lys Gly Asp
                    325                 330                 335
    Cys Tyr Asp Arg Tyr Leu Cys Arg Val Glu Glu Met Arg Gln Ser Leu
                    340                 345                 350
    Asn Ile Val His Gln Cys Leu Asn Lys Met Pro Thr Gly Glu Ile Lys
                    355                 360                 365
    Ser Asp Asp His Lys Val Val Pro Pro Lys Arg Ala Glu Met Lys Glu
            370                 375                 380
    Asn Met Glu Ser Leu Ile His His Phe Lys Phe Phe Thr Glu Gly Phe
    385                 390                 395                 400
    Gln Val Pro Pro Gly Ala Thr Tyr Val Pro Ile Glu Ala Pro Lys Gly
                    405                 410                 415
    Glu Phe Gly Val Tyr Leu Val Ala Asp Gly Thr Gly Lys Pro Tyr Arg
                    420                 425                 430
    Cys Phe Ile Arg Ala Pro Gly Phe Ala His Leu Ala Ala Ile His Asp
                    435                 440                 445
    Val Cys Tyr Met Ser Leu Ile Ala Asp Ile Val Ala Val Ile Gly Thr
            450                 455                 460
    Met Asp Ile Val Phe Gly Glu Val Asp Arg
    465                 470
```

(2) INFORMATION FOR SEQ ID NO:7:

(i) SEQUENCE CHARACTERISTICS:
        (A) LENGTH: 82 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 560

(xi) SEQUENCE DESCRIPTION: SEQ ID NO:7:

```
Met Leu Arg Gln Ile Ile Gly Gln Ala Lys Arg His Pro Ser Leu Ile
1               5                   10                  15
Pro Leu Phe Ile Phe Ile Gly Ala Gly Gly Thr Gly Ala Ala Leu Tyr
                20                  25                  30
Val Thr Arg Leu Ala Leu Phe Asn Pro Asp Val Ser Trp Asp Arg Lys
            35                  40                  45
Asn Asn Pro Glu Pro Trp Asn Lys Leu Gly Pro Asn Asp Gln Tyr Lys
        50                  55                  60
Phe Tyr Ser Val Asn Val Asp Tyr Ser Lys Leu Lys Lys Glu Gly Pro
65                  70                  75                  80
Asp Phe
```

(2) INFORMATION FOR SEQ ID NO:8:

(i) SEQUENCE CHARACTERISTICS:
        (A) LENGTH: 75 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1401252

(xi) SEQUENCE DESCRIPTION: SEQ ID NO:8:

Gln Ala Lys Lys His Pro Ser Leu Ile Pro Leu Phe Val Phe Ile Gly

-continued

```
1               5               10              15
Ala Gly Gly Thr Gly Ala Ala Leu Tyr Val Met Arg Leu Ala Leu Phe
            20              25              30

Asn Pro Asp Val Ser Trp Asp Arg Lys Asn Asn Pro Glu Pro Trp Asn
        35              40              45

Lys Leu Gly Pro Asn Glu Gln Tyr Lys Phe Tyr Ser Val Asn Val Asp
    50              55              60

Tyr Ser Lys Leu Lys Lys Glu Gly Pro Asp Phe
65              70              75
```